(12) United States Patent
Takahashi et al.

(10) Patent No.: US 7,426,850 B2
(45) Date of Patent: Sep. 23, 2008

(54) OUTER CASING FOR GAS SENSOR

(75) Inventors: Ikuo Takahashi, Tokorozawa (JP); Junji Satoh, Kawagoe (JP); Hiroto Matsuda, Higashimurayama (JP)

(73) Assignee: Citizen Holdings Co., Ltd., Tokyo (JP)

( * ) Notice: Subject to any disclaimer, the term of this patent is extended or adjusted under 35 U.S.C. 154(b) by 100 days.

(21) Appl. No.: 11/092,575

(22) Filed: Mar. 29, 2005

(65) Prior Publication Data

US 2005/0217370 A1 Oct. 6, 2005

(30) Foreign Application Priority Data

| Mar. 30, 2004 | (JP) | ............................... 2004-097311 |
| Sep. 28, 2004 | (JP) | ............................... 2004-281013 |
| Jan. 27, 2005 | (JP) | ............................... 2005-019197 |

(51) Int. Cl.
    *G01N 7/00* (2006.01)
(52) U.S. Cl. ..................................... 73/31.05
(58) Field of Classification Search .................. 73/431, 73/25.01, 25.05, 31.05, 31.06; 422/94–97
    See application file for complete search history.

(56) References Cited

U.S. PATENT DOCUMENTS

| 3,715,636 | A | * | 2/1973 | Jaffe et al. ..................... 257/76 |
| 5,121,627 | A | * | 6/1992 | D'Aoust ..................... 73/19.05 |
| 5,535,614 | A | * | 7/1996 | Okamoto et al. ........... 73/23.31 |
| 5,895,591 | A | * | 4/1999 | Kojima et al. ............... 219/209 |
| 5,918,260 | A | * | 6/1999 | Newman et al. ........... 73/31.05 |
| 5,922,938 | A | * | 7/1999 | Hafele ........................ 73/23.32 |
| 2005/0025215 | A1 | * | 2/2005 | Arndt et al. ................... 374/44 |
| 2005/0042141 | A1 | * | 2/2005 | Otani et al. ................... 422/98 |

FOREIGN PATENT DOCUMENTS

JP 55-082954 A 6/1980

* cited by examiner

*Primary Examiner*—Robert R Raevis
(74) *Attorney, Agent, or Firm*—Foley & Lardner LLP

(57) ABSTRACT

An outer casing for a gas sensor includes a cap, a mount base, and a heat shielding board. The cap, the mount base, and the heat shielding board are made of gas permeable ceramics. A target gas flows inside the gas sensor with the above outer casing from all directions, and makes the gas sensor highly responsive to the target gas. The outer casing also contributes to make temperature and humidity inside the gas sensor uniform in a short time, thereby stabilizing an output voltage of the gas sensor.

18 Claims, 9 Drawing Sheets

OUTER CASING FOR GAS SENSOR

BACKGROUND OF THE INVENTION

1) Field of the Invention

The present invention relates to an outer casing for a flammable gas sensor.

2) Description of the Related Art

Conventionally, a catalytic combustion type gas sensor and a semiconductor type gas sensor are used as a gas sensor for detecting flammable gas, such as hydrogen and methane. Both types of the gas sensors include a heat source that is used for detecting the flammable gas. For example, the catalytic combustion type gas sensor includes a heater coil with a combustion catalyst as the heat source. The flammable gas causes combustion with the catalyst. The heat generated by the combustion causes a change in resistance of the heater coil, and the change is output as a change in voltage of the gas sensor. Thus, the flammable gas is detected.

On the other hand, the semiconductor type gas sensor includes a heater coil with a semiconductor layer. The semiconductor layer absorbs the flammable gas, and electrical conductivity thereof changes according to the absorption. The change is output as a change in voltage of the gas sensor. Thus, the flammable gas is detected.

The above gas sensors have a gas permeable cap to stabilize temperature equilibrium of the heater coil and to prevent explosion of the flammable gas. The gas permeable cap is made of wire gauze, sintered metal, porous ceramics, and the like. Such a technology is disclosed in, for example, Japanese Patent Application Laid-Open No. S55-82954.

The above gas sensors also have a mount base that is made of synthetic resin without gas permeability. The mount base supports a charging unit including pin electrodes, which pierce through the mount base and are electrically connected to a gas sensing element. The catalytic combustion type gas sensor also includes a compensating element that has the same temperature-equilibrium property as the gas sensing element. When the gas sensing element and the compensating element are arranged in a single housing, a heat shielding board that is made of metal or synthetic resin is arranged between the elements to avoid temperature interference, and to keep temperature and humidity uniform around the elements.

The gas permeable cap has a function of protecting the gas sensing element from various environmental factors. However, the gas permeable cap can decrease sensitivity of the gas sensor because gas permeability of the gas permeable cap is limited. The mount base does not contribute to the sensitivity because the mount base does not permeate a target gas inside the gas sensor.

Moreover, the heat shielding board, which is provided in the catalytic combustion type gas sensor to insulate heat between the gas sensing element and the compensating element, shields atmosphere between the elements inside the gas sensor. This is not preferable for stabilizing output voltage of the gas sensor according to temperature and humidity.

Furthermore, the gas permeable cap made of wire gauze, sintered metal, or conventional porous ceramics does not have resistance to a gas, such as an organic solvent gas, that can deteriorate the gas-detection function of the gas sensor. Therefore, additional equipment such as a supplemental filter of activated carbon is required to remove the gas. This increases a manufacturing cost of the gas sensor. Moreover, it is necessary to consider corrosion resistance if a metallic part is included in the gas permeable cap.

SUMMARY OF THE INVENTION

It is an object of the present invention to solve at least the above problems in the conventional technology.

An outer casing for a gas sensor according to an aspect of the present invention includes a cap for protecting a plurality of elements from any one of wind and explosion; pin electrodes that are electrically connected to the elements; a mount base that supports the pin electrodes; and a heat shielding board that separates space surrounded by the cap and the mount base for insulating heat from each of the elements. The cap, the mount base, and the heat shielding board are made of ceramics.

An outer casing for a gas sensor according to another aspect of the present invention includes a cap for protecting a plurality of elements from any one of wind and explosion; pin electrodes that are electrically connected to the elements; a mount base that supports the pin electrodes; and a heat shielding board that separates space surrounded by the cap and the mount base for insulating heat from each of the elements. Each of the pin electrodes includes a rough surface, and is fixed to the mount base with an adhesive in such a manner that each of the pin electrodes pierces through the mount base. The adhesive is a mixture of glass and any one of alumina ceramics, alumina-zirconia ceramics, and alumina-diatomaceous earth ceramics.

A gas sensor according to still another aspect of the present invention includes a sensing element for detecting a target gas; a compensating element for stabilizing an output of the gas sensor; a cap for protecting the sensing element and the compensating element from any one of wind and explosion; pin electrodes that are electrically connected to any one of the sensing element and the compensating element; a mount base that supports the pin electrodes; and a heat shielding board that separates space surrounded by the cap and the mount base for insulating heat from the sensing element and the compensating element. The cap, the mount base, and the heat shielding board are made of ceramics.

The other objects, features, and advantages of the present invention are specifically set forth in or will become apparent from the following detailed description of the invention when read in conjunction with the accompanying drawings.

DETAILED DESCRIPTION

Figure 1:
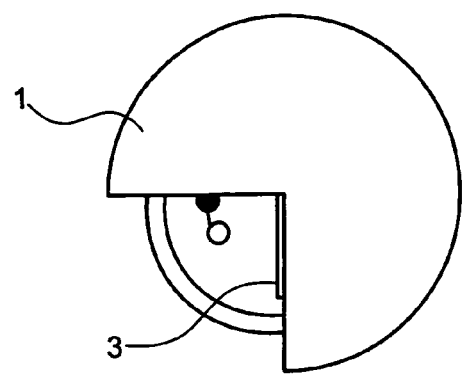
FIG. 1 is a plan view of an outer casing for a gas sensor according to a first embodiment of the present invention.

Exemplary embodiments of the present invention will be explained in detail with reference to the accompanying drawings. Like reference numerals refer to like parts throughout the drawings, and redundant explanation is omitted.

Figure 2:
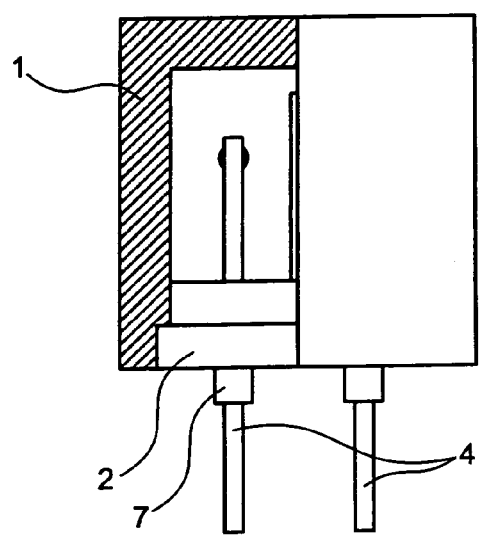
FIG. 2 is a front view of the outer casing shown in FIG. 1.
Figure 3:
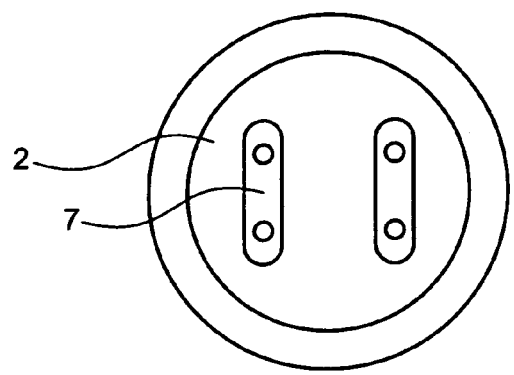
FIG. 3 is a bottom view of the outer casing shown in FIG. 1.
Figure 4:
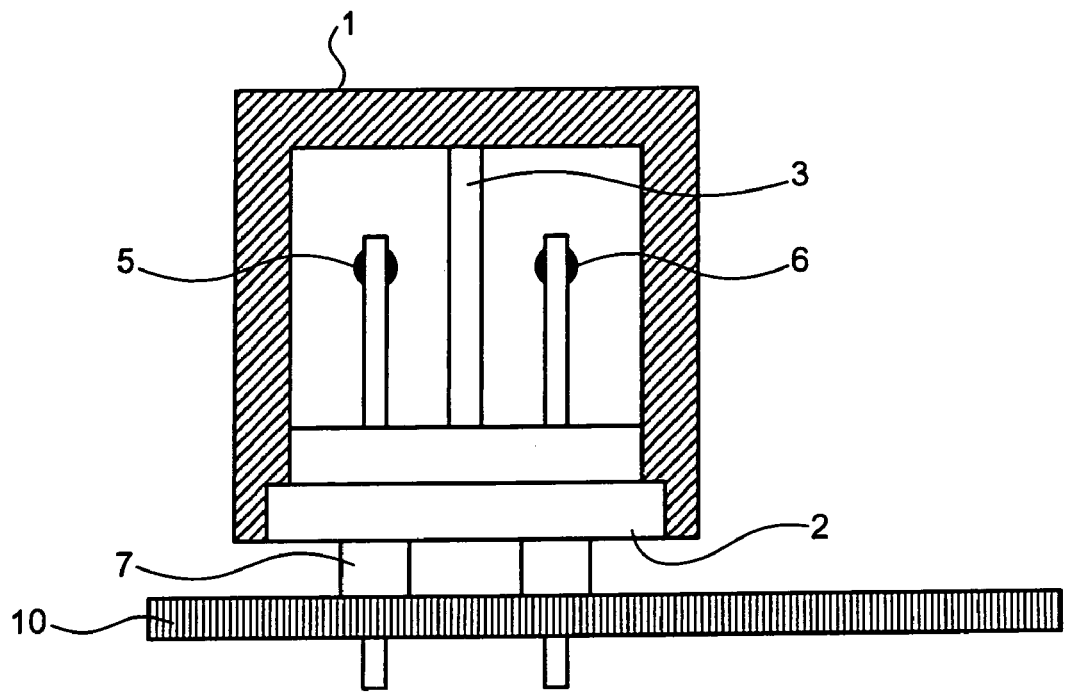
FIG. 4 is a cross section of the outer casing shown in FIG. 1.
Figure 5:
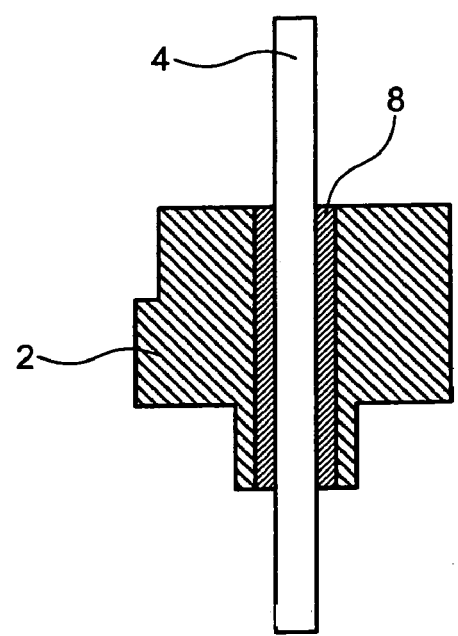
FIG. 5 is another cross section of the outer casing shown in FIG. 1.
Figure 6:
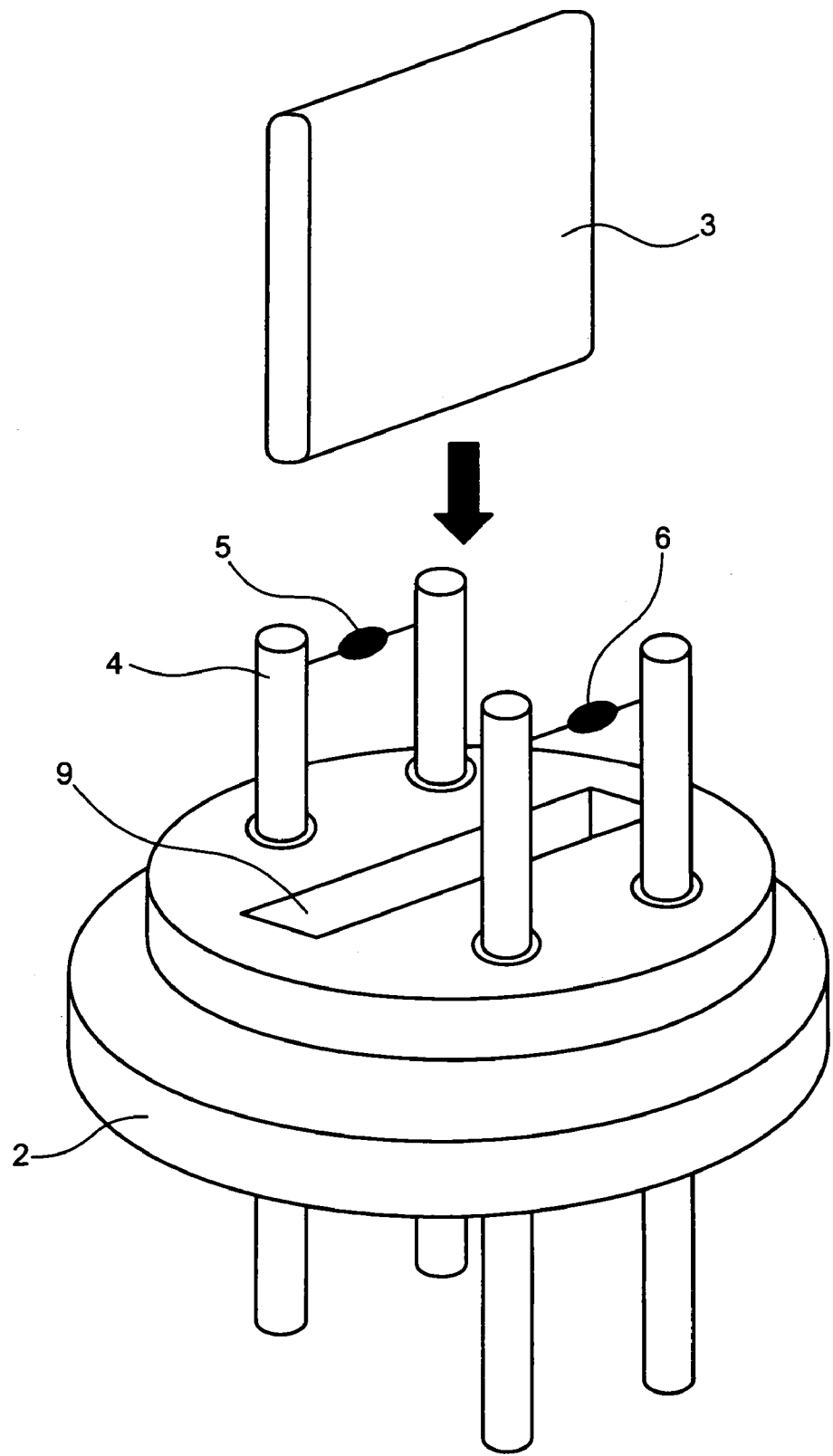
FIG. 6 is a perspective view of the outer casing for explaining installation of a heat shielding board.

FIGS. 1 to 4 are schematics of an outer casing for a gas sensor according to a first embodiment of the present invention. FIGS. 5 and 6 are detailed schematics of a pin electrode and a heat shielding board of the outer casing. FIGS. 1 and 2 are cutaway views in which a cap of the outer casing is partially cut away to show the inside of the gas sensor.

According to the first embodiment, the outer casing includes a cap 1, a mount base 2, and a heat shielding board 3. The cap 1, the mount base 2, and the heat shielding board 3 are made of ceramics with gas permeability, such as alumina-diatomaceous earth ceramics, which includes alumina and diatomaceous dispersed therein. The cap 1, the mount base 2, and the heat shielding board 3 are adhered to each other with a glass material, for example, a glass adhesive. As shown in FIG. 5, a pin electrode 4 pierces through a through-hole of the mount base 2, and is adhered to the mount base 2 with a glass adhesive 8. For example, a catalytic combustion type gas sensor includes four pin electrodes 4, two of which are connected to a sensing element 5, and another two of which are connected to a compensating element 6.

The surface of the pin electrode 4 is surrounded by a pin base 7 that is arranged on the underside of the mount base 2. As shown in FIG. 4, the pin base 7 provides a space between the mount base 2 and a control circuit board 10, thereby allowing a target gas to flow into the gas sensor through the mount base 2 (in other words, from the underside of the gas sensor).

Response times of catalytic combustion type gas sensors are shown in table 1. "Response time" means time required for an output signal of a gas sensor to become stable for 90 percent (%) in a target gas of 4,000 parts per million (ppm). "Example 1 (all ceramics)" shown in table 1 represents a gas sensor with a cap and a mount base that are made of gas permeable ceramics. "Example 2 (cap only)" represents a gas sensor with a cap made of gas permeable ceramics and a mount base without gas permeability. "Conventional example (wire gauze cap)" represents a gas sensor with a cap of wire gauze and a mount base without gas permeability.

TABLE 1 response time for target gas of 4,000 ppm

|  | Hydrogen (second) | Methane (second) |
|---|---|---|
| Example 1 (all ceramics) | 2 | 3 |
| Example 2 (cap only) | 4 | 6 |
| Conventional example (wire gauze cap) | 3 | 5 |

As shown in table 1, the response time of example 1 is shorter than those of example 2 and the conventional example, because the outer casing of example 1 allows the target gas to flow into the gas sensor from all directions.

Gas sensitivity of catalytic combustion type gas sensors with respect to ethanol are shown in table 2. "Gas sensitivity" is a difference between an output voltage of a gas sensor in ethanol-containing air and an output voltage of the gas sensor in clean air (that is, in non-ethanol-containing air). "Example 1 (all ceramics)" shown in table 2 represents a gas sensor with a cap and a mount base that are made of gas permeable ceramics such as the alumina-diatomaceous earth ceramics. "Conventional example (wire gauze cap)" represents a gas sensor with a cap of wire gauze and a mount base of synthetic resin.

TABLE 2 gas sensitivity to ethanol of 1,000 ppm

|  | Gas sensitivity (mV) |
|---|---|
| Example 1 (all ceramics) | 8 |
| Conventional example (wire gauze cap) | 20 |

Gas sensitivity to ethanol of a gas sensor for hydrogen, methane, and the like should be as low as possible because ethanol is not a target gas in such a gas sensor. As shown in table 2, the gas sensitivity to ethanol of example 1 is lower than that of the conventional example. In other words, the gas sensor of example 1 has a superior property in non-permeability for ethanol. A gas sensor with a cap and a mount base that are made of the alumina-zirconia ceramics is equivalent to the gas sensor of example 1. Other organic solvent gases do not flow into such gas sensors because diatomaceous earth or zirconia, which is dispersed in an alumina base, absorbs the organic solvent gases.

Protectivity from wind of the catalytic combustion type gas sensors are shown in table 3. "Example 1 (all ceramics)" represents a gas sensor with a cap, a mount base, and a heat shielding board that are made of gas permeable ceramics. "Conventional example (wire gauze cap)" represents the gas sensor with the cap of wire gauze and the mount base of synthetic resin. In the test shown in table 3, wind of 1 meter/second (m/s), 3 m/s, and 5 m/s are respectively applied to the gas sensors from a direction of the sensing element.

TABLE 3 zero-point fluctuation value converted into hydrogen concentration

|  | Velocity (m/s) | | |
|---|---|---|---|
|  | 1 | 3 | 5 |
| Example 1 (all ceramics) (ppm) | 20 | 110 | 200 |
| Conventional example (wire gauze cap) (ppm) | 200 | 500 | 1,000 |

The zero-point fluctuation value under influence of wind, whose velocity is equal to or smaller than 0.1 m/s, is approximately 200 ppm. As shown in table 3, the zero-point fluctuation due to wind is smaller in example 1 that the conventional example. In other words, the velocity of the wind inside the gas sensor is decreased in example 1.

Moreover, a test for an explosionproof property was conducted with the gas sensor of example 1 shown in table 3. Even in air containing 4% hydrogen, which is the lower explosion limit of hydrogen, an explosion was not caused in a test system. Thus, the gas sensor has an excellent explosion-proof property.

As shown in FIG. 6, the heat shielding board 3 is set in a fixing groove 9 that is arranged in the mount base 2. In the first embodiment, the heat shielding board 3 is manufactured separately from the mount base 2, and the heat shielding board 3 is adhered to the fixing groove 9 of the mount base 2 with the glass adhesive 8. The fixing groove 9 enables accurate positioning of the heat shielding board 3 on the mount base 2.

The fixing groove 9 can be left unused in the semiconductor type gas sensor in which the heat shielding board 3 is not required. In other words, the outer casing for a gas sensor according to the first embodiment can be used for both the catalytic combustion type gas sensor and the semiconductor type gas sensor.

The catalytic combustion type gas sensor detects the target gas based on the output voltage of the sensing element 5. The output voltage changes according to the resistance of a heather coil therein, and the resistance changes according to heat generated by the catalytic combustion of the target gas. However, heat radiated from the compensating element 6 can also change the resistance. Therefore, the heat shielding board 3 is necessary between the sensing element 5 and the compensating element 6 to prevent the radiated heat from changing the resistance. On the other hand, it is preferable that the sensing element 5 and the compensating element 6 should exist in the same temperature and the same humidity as possible, because the compensating element 6 is provided to stabilize the output voltage of the gas sensor by retarding reaction thereof to a change in the temperature and the humidity.

The heat shielding board 3 according to the first embodiment can prevent heat radiated from the sensing element 5 and the heat radiated from the compensating element 6 from interfering with each other. Furthermore, a gas can flow between the space in which the sensing element 5 is arranged and the space in which the compensating element 6 is arranged, through the heat shielding board 3 which is made of porous ceramics and thereby gas permeable. Therefore, the temperature and the humidity in both the spaces become uniform or close to uniform. Furthermore, resistance of the gas sensor to environmental conditions can also be increased because the outer casing made of ceramics are resistant to acids and alkalis.

Figure 7:
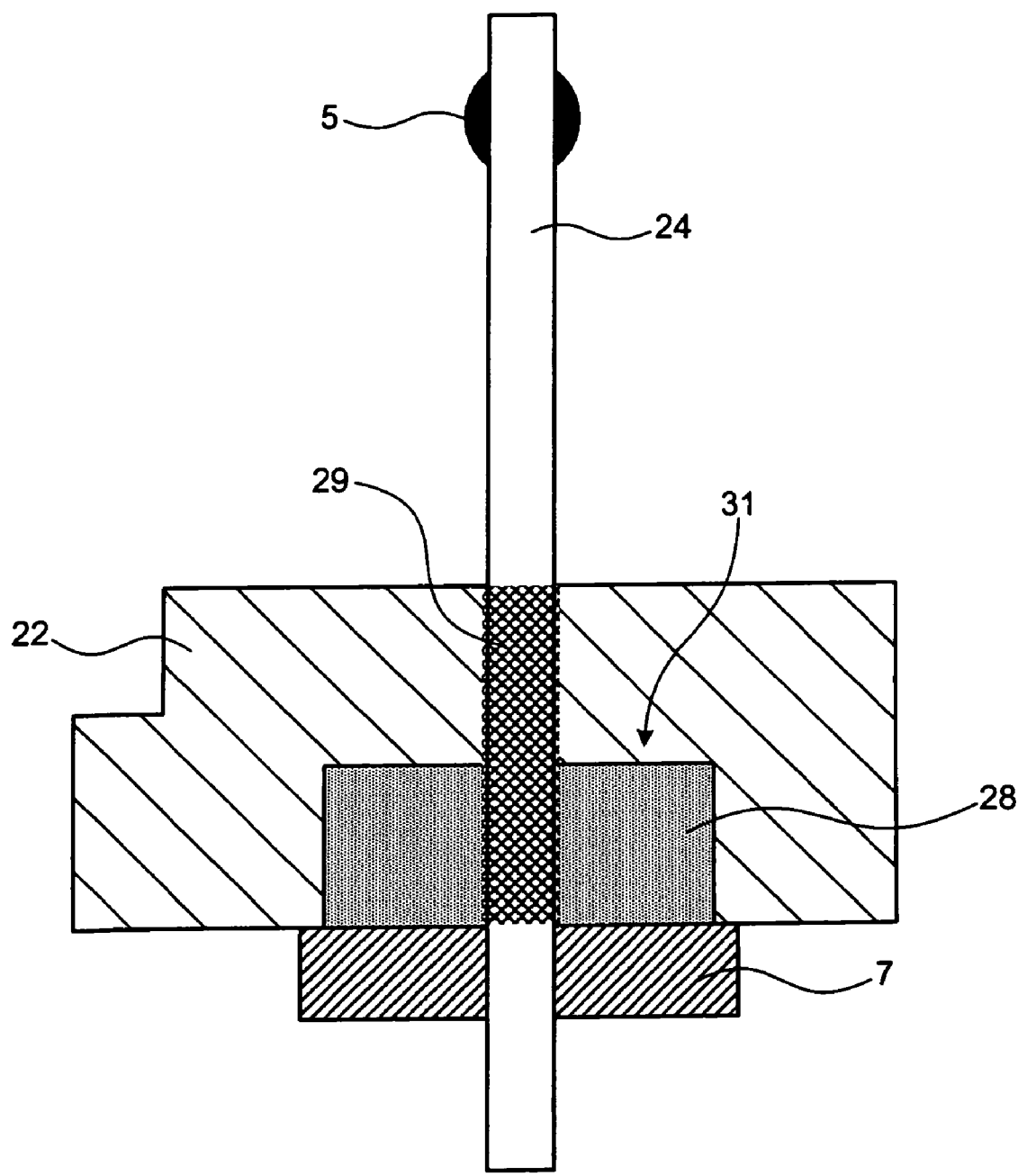
FIG. 7 is a cross section of an outer casing for a gas sensor according to a second embodiment of the present invention.

FIG. 7 is a cross section of an outer casing for a gas sensor according to a second embodiment of the present invention, showing a portion where a pin electrode is fixed in detail. As shown in FIG. 7, the outer casing according to the second embodiment includes a mount base 22, which is made of gas permeable ceramics and has a concave section 31, instead of the mount base 2. The outer casing also includes a pin electrode 24, instead of the pin electrode 4. The mount base 22 and the pin electrode 24 are adhered by a mixture adhesive 28 that includes ceramics and glass, instead of the glass adhesive 8.

The pin electrode 24 includes a rough surface 29 that is formed, for example, by knurling. As shown in FIG. 7, the rough surface 29 is arranged at a portion to be fit inside the mount base 22. The concave section 31 is arranged on one side of the mount base 22 at a portion where the pin electrode 24 pierces through. The mixture adhesive 28 is filled in the concave section 31 to fix the pin electrode 24 piercing through the mount base 22.

The glass included in the mixture adhesive 28 is softened when its temperature reaches the glass transition temperature, thereby causing ceramics particles in the mixture adhesive 28 to be combined with each other. The glass softened flows into porous structure of the mount base 22 and pits of the rough surface 29 of the pin electrode 24. Thus, the mixture adhesive 28 itself becomes porous while keeping adhesion between the pin electrode 24 and the mount base 22.

The pin base 7 is arranged to seal the concave section 31 filled with the mixture adhesive 28. The pin base 7 prevents the softened glass in the mixture adhesive 28 from soaking outside the gas sensor.

The mount base 22, the pin electrode 24, and the pin base 7 become firmly connected to each other by the mixture adhesive 28 filled in the concave section 31, when the temperature of the mixture adhesive 28 reaches the glass transition temperature. It is preferable that a ratio of glass to be contained in the mixture adhesive 28 is 30 mol % or less. In the following explanations, it is assumed that the ratio is 4 mol %, and glass contained in the mixture adhesive 28 has a low melting point of 800 degree Celsius (° C.).

Response time of catalytic combustion type gas sensors in a target gas of 4,000 ppm are shown in table 4. "Example 1 (alumina ceramics and glass)" represents a gas sensor with mixture adhesive including alumina ceramics. "Example 2 (alumina-zirconia ceramics and glass)" represents a gas sensor with mixture adhesive including alumina-zirconia ceramics. "Example 3 (alumina-diatomaceous earth ceramics)" represents a gas sensor with mixture adhesive including alumina-diatomaceous earth ceramics. "Example for comparison (only glass)" represents a gas sensor with conventional adhesive including glass only.

TABLE 4

| response time for target gas of 4,000 ppm (ratio of glass contained is 4 mol %) | | |
| --- | --- | --- |
| | Hydrogen (second) | Methane (second) |
| Example 1 (alumina ceramics and glass) | 1.5 | 2.5 |
| Example 2 (alumina-zirconia ceramics and glass) | 1.5 | 2.5 |
| Example 3 (alumina-diatomaceous earth ceramics and glass) | 1.5 | 2.5 |
| Example for comparison (glass only) | 2 | 3 |

As shown in table 4, the response time of any of examples 1 to 3 is shorter than that of the example for comparison, because the mixture adhesive becomes porous, thereby allowing the target gas to flow into the gas sensor more easily.

Pull-out strength of the pin electrode 24 that is fixed to the mount base 22 in the catalytic combustion type gas sensors are shown in table 5. "Pull-out strength" means a load that is required to pull out the pin electrode 24 fixed in the through-hole of the mount base 22 with an adhesive. "Example 1 (alumina ceramics and glass)", "example 2 (alumina-zirconia ceramics and glass)", "example 3 (alumina-diatomaceous earth ceramics)", and "example for comparison (only glass)" shown in table 5 have the same structure as the examples shown in table 4, respectively.

TABLE 5

| pull-out strength (ratio of glass contained is 4 mol %) | |
| --- | --- |
| | Load (N) |
| Example 1 (alumina ceramics and glass) | 200 or more |
| Example 2 (alumina-zirconia ceramics and glass) | 200 or more |
| Example 3 (alumina-diatomaceous earth ceramics and glass) | 200 or more |
| Example for comparison (glass only) | 150 |

As shown in table 5, the pull-out strength of any of examples 1 to 3 is higher than that of the example for comparison, because the adhesive softened and strengthened at the glass transition temperature flows into the pits of the rough surface 29 on the pin electrode 24 and the porous structure of the mount base 22, to firmly adhere the pin electrode 24 to the mount base 22.

In the gas sensor of the example for comparison, thermal expansion coefficient of each of the mount base 22 made of ceramics, the pin electrode 24 made of metal, and the adhesive made of glass without ceramics, is different from each other. Therefore, when the gas sensor is exposed to high temperatures, the intimate contact between the pin electrode 24 and the adhesive can be lost. As a result, the pin electrode 24 comes apart from the mount base 22, for example, during installation of the pin electrode 24 to the control circuit board 10. According to the second embodiment, it is possible to prevent the pin electrode 24 from coming apart from the mount base 22 because the pull-out strength of the pin electrode 24 is high.

Figure 8:
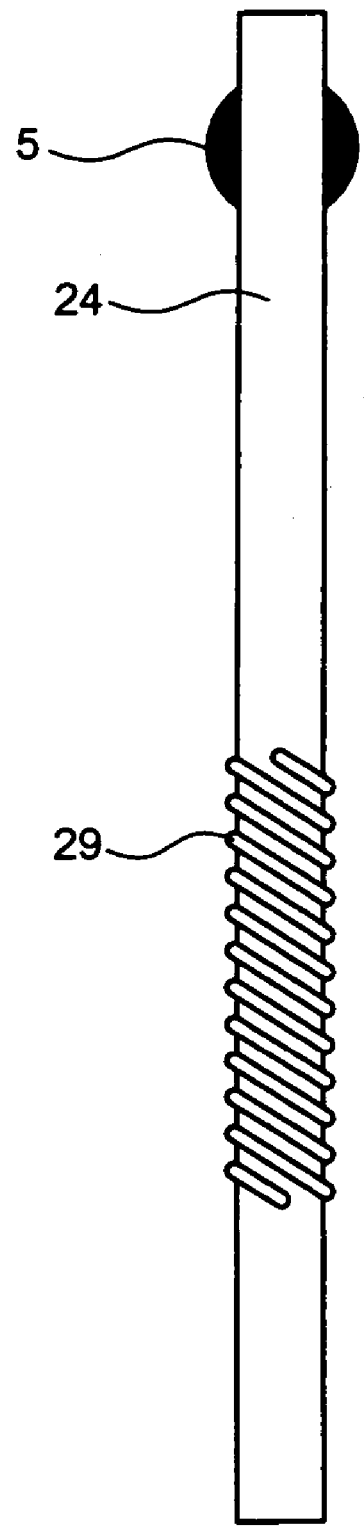
FIG. 8 is a schematic of a modification of a pin electrode according to the second embodiment.
Figure 9:
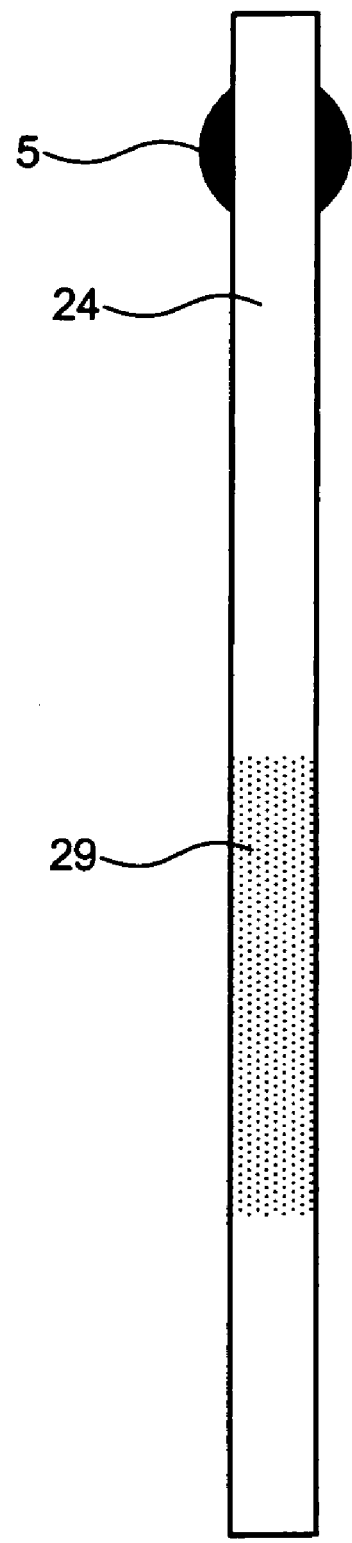
FIG. 9 is a schematic of another modification of the pin electrode.
Figure 10:
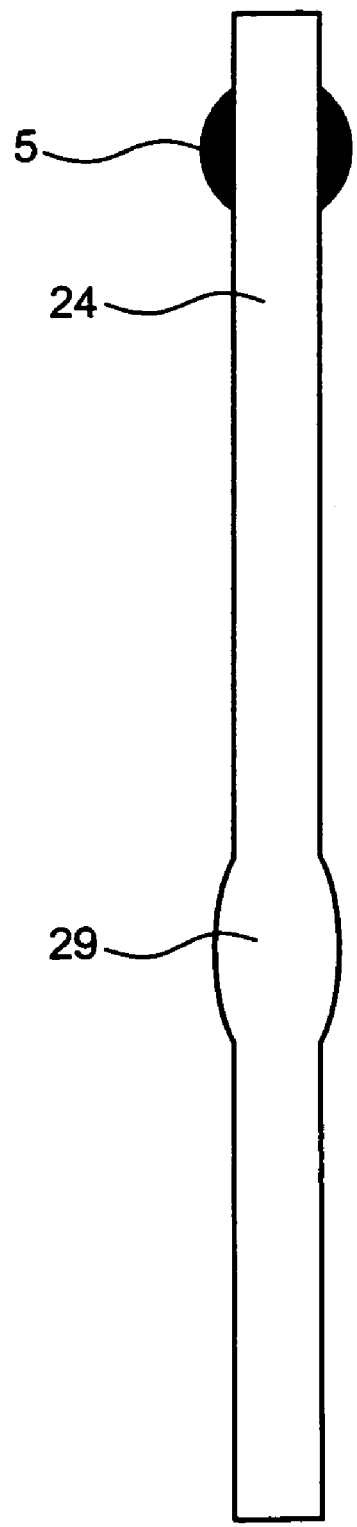
FIG. 10 is a schematic of still another modification of the pin electrode.
Figure 11:
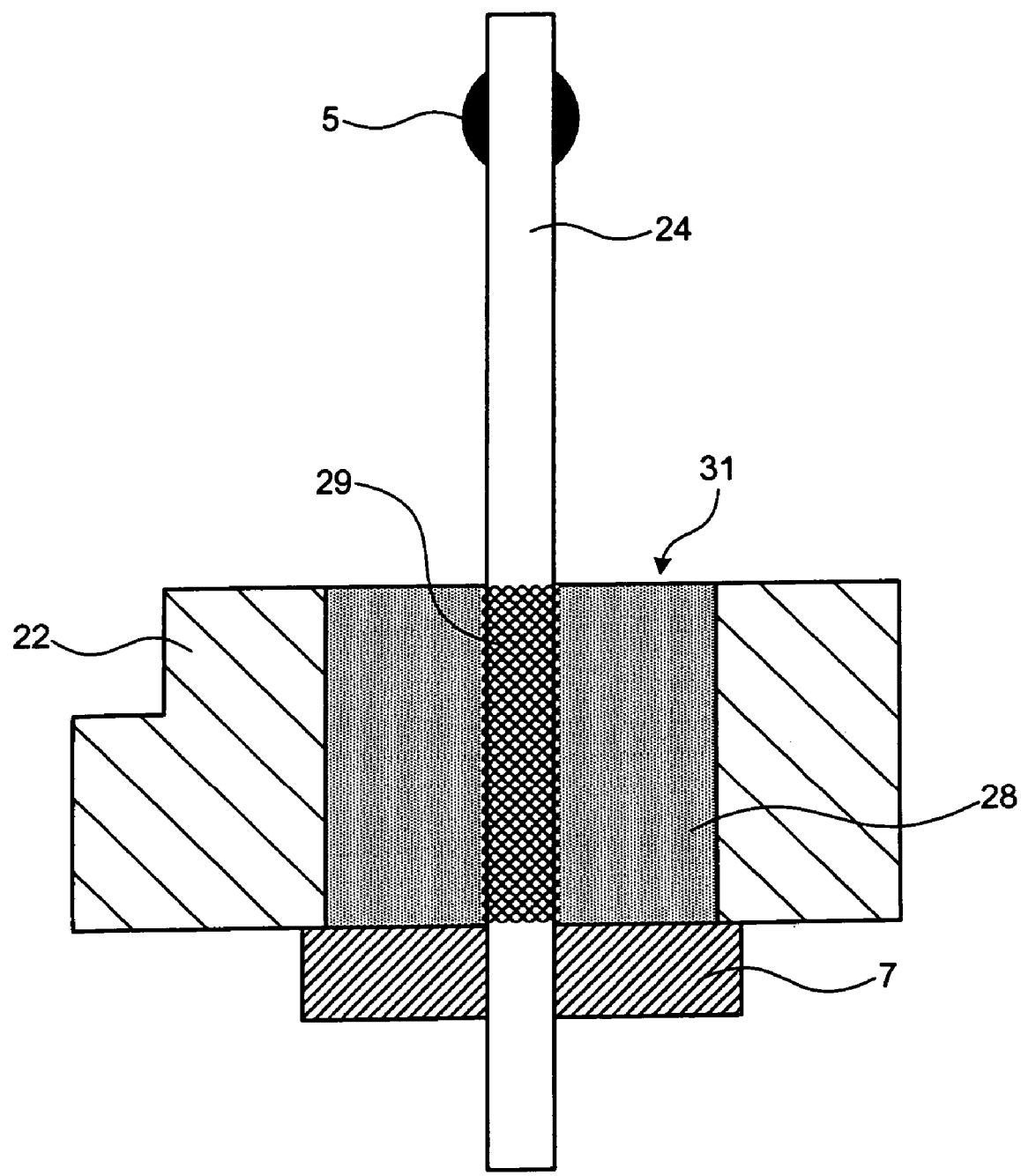
FIG. 11 is a cross section of a modification of the outer casing.
Figure 12:
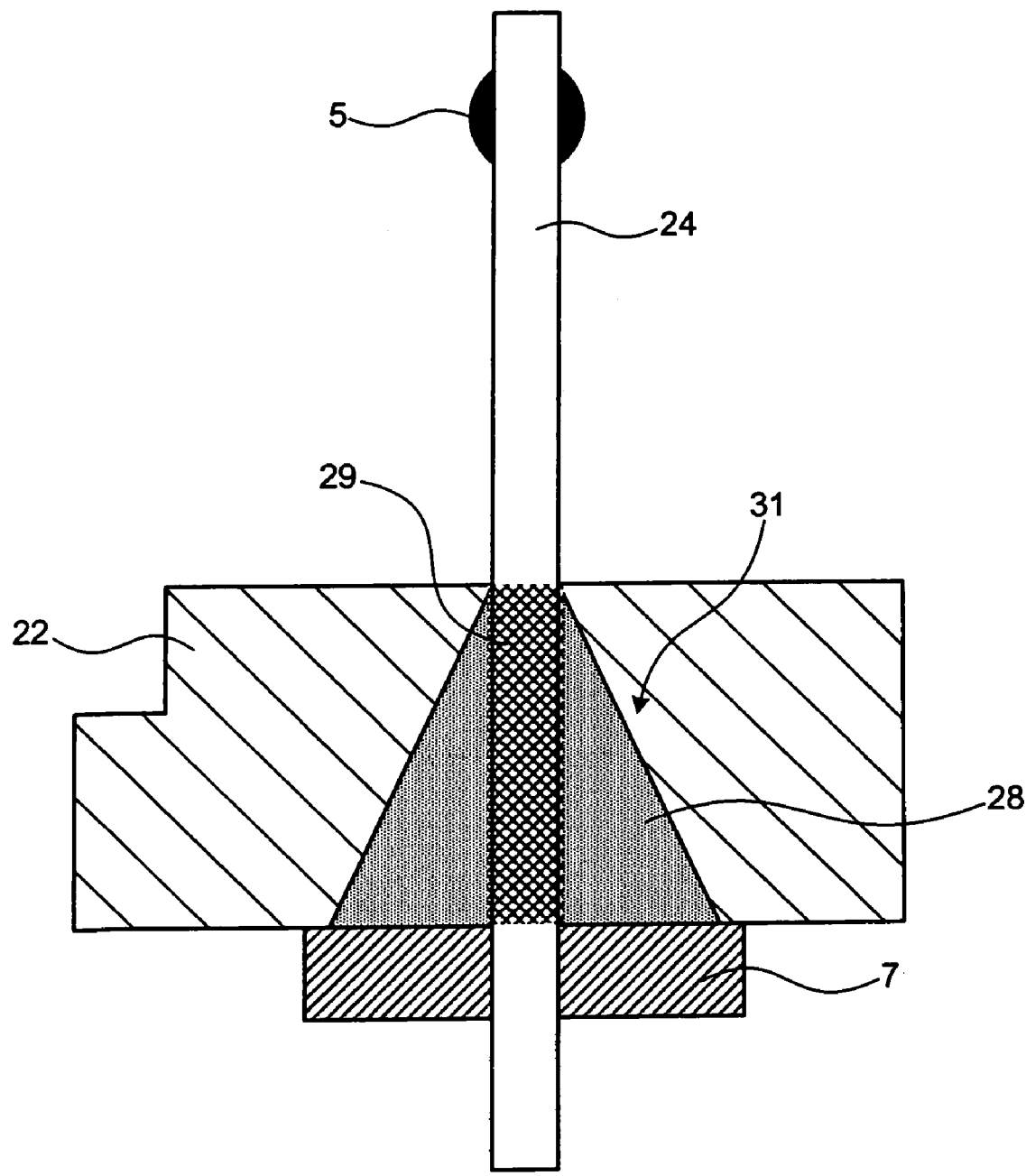
FIG. 12 is a cross section of another modification of the outer casing.

The rough surface 29 can be formed as a surface that has a groove or a projection similar to thread-cutting as shown in FIG. 8, a matte surface as shown in FIG. 9, or a pressed surface that is flattened and stretched by applying pressure with pliers as shown in FIG. 10. On the other hand, the concave section 31 of the mount base 22 can be formed in a hollow that is open through the mount base 22 around the pin electrode 24 as shown in FIG. 11, or in a cone-shaped hollow as shown in FIG. 12 to make it easy to position the pin electrode 24 without a lean. With any of the modifications shown in FIGS. 8 to 12, high pull-out strength can be obtained.

According to the present invention, it is possible to obtain a gas sensor that has excellent responsivity, high stability, excellent explosionproof property, and preferable property to non-target gases. Moreover, it is possible to stabilize the explosionproof property of a gas sensor, and to stabilize output signals of the gas sensor. It is also possible to realize a sturdy gas sensor.

The present document incorporates by reference the entire contents of Japanese priority document, 2004-97311, 2004-281013 and 2005-019197 filed in Japan on Mar. 30, 2004, Sep. 28, 2004 and Jan. 27, 2005.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. A gas sensor, comprising:
   a cap for protecting a sensor element from any one of wind and explosion;
   pin electrodes that are electrically connected to the sensor element;
   a mount base that supports the pin electrodes; and
   a heat shielding board that separates space surrounded by the cap and the mount base for insulating heat from the sensor element;
   wherein the cap and the mount base are made of ceramic;
   wherein the ceramic is a porous ceramic.

2. The gas sensor according to claim 1, wherein the heat shielding board is made of a porous ceramic.

3. The gas sensor according to claim 1, wherein the cap is made of any one of alumina ceramics, alumina-zirconia ceramics, and alumina-diatomaceous earth ceramics.

4. The gas sensor according to claim 1, wherein the mount base is made of any one of alumina ceramics, alumina-zirconia ceramics, and alumina-diatomaceous earth ceramics.

5. The gas sensor according to claim 1, wherein the cap is made of material that does not allow an organic solvent gas to permeate.

6. The gas sensor according to claim 1, wherein the mount base is made of material that does not allow an organic solvent gas to permeate.

7. The gas sensor according to claim 1, further comprising a compensating element electrically connected to another set of pin electrodes.

8. The gas sensor according to claim 1, wherein the mount base includes a groove to which the heat shielding board could be fixed.

9. A gas sensor, comprising:
   a cap for protecting a sensor element from any one of wind and explosion;
   pin electrodes that are electrically connected to the sensor element; and
   a mount base that supports the pin electrodes;
   wherein each of the pin electrodes includes a rough surface, and is fixed to the mount base with an adhesive in such a manner that each of the pin electrodes pierces through the mount base, and
   the adhesive is a mixture of glass and any one of alumina ceramics, alumina-zirconia ceramics, and alumina-diatomaceous earth ceramics.

10. The gas sensor according to claim 9, wherein the mount base includes a concave section in which the adhesive is filled.

11. The gas sensor according to claim 9, wherein the mount base includes a hollow in which the adhesive is filled, wherein the hollow is open through the mount base around a pin electrode.

12. The gas sensor according to claim 9, further comprising:
   a heat shielding board that separates space surrounded by the cap and the mount base for insulating heat from the sensor element.

13. The gas sensor according to claim 9, wherein the rough surface is a thread-cutting surface.

14. The gas sensor according to claim 9, wherein the rough surface is a matte surface.

15. The gas sensor according to claim 9, wherein the rough surface is a pressed surface.

16. A gas sensor comprising:
   a sensing element for detecting a target gas;
   a compensating element for stabilizing an output of the sensing element;
   a cap for protecting the sensing element and the compensating element from any one of wind and explosion;
   pin electrodes that are electrically connected to any one of the sensing element and the compensating element;
   a mount base that supports the pin electrodes; and
   a heat shielding board that separates space surrounded by the cap and the mount base for insulating heat from the sensing element and the compensating element, wherein the cap, the mount base, and the heat shielding board are made of ceramics;
   wherein the ceramics is porous ceramics.

17. A gas sensor, comprising:
   a cap for protecting a sensor element;
   a mount base that is configured to support pin electrodes electrically connected to the sensor element; and
   a heat shielding board that separates space surrounded by the cap and the mount base for insulating heat from the sensor element;
   wherein the cap and the mount base are made of ceramic;
   wherein the ceramic is porous ceramic.

18. The gas sensor of claim 17, wherein the heat shielding board is made of a porous ceramic.

* * * * *